(12) United States Patent
Zamloot et al.

(10) Patent No.: US 9,339,463 B2
(45) Date of Patent: May 17, 2016

(54) MICRONIZED OPIOID COMPOSITIONS HAVING A SPECIFIC PARTICLE SIZE DISTRIBUTION

(76) Inventors: Michael Zamloot, Hillsborough, CA (US); Cherng-chyi Fu, Saratoga, CA (US); De-Hwa Chao, Cupertino, CA (US); Andrei Blasko, San Bruno, CA (US); Su Il Yum, Cupertino, CA (US)

( * ) Notice: Subject to any disclaimer, the term of this patent is extended or adjusted under 35 U.S.C. 154(b) by 189 days.

(21) Appl. No.: 12/329,318

(22) Filed: Dec. 5, 2008

(65) Prior Publication Data

US 2009/0169631 A1    Jul. 2, 2009

Related U.S. Application Data

(60) Provisional application No. 61/110,855, filed on Nov. 3, 2008, provisional application No. 61/012,033, filed on Dec. 6, 2007.

(51) Int. Cl.
| | |
|---|---|
| *A61K 9/14* | (2006.01) |
| *A61P 25/04* | (2006.01) |
| *A61K 9/16* | (2006.01) |
| *A61K 31/485* | (2006.01) |

(52) U.S. Cl.
CPC ............. *A61K 9/14* (2013.01); *A61K 9/1623* (2013.01); *A61K 9/1652* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 6,190,680 B1 | 2/2001 | Sakurada et al. | |
| 2004/0115134 A1* | 6/2004 | Merisko-Liversidge | ....... 424/45 |
| 2005/0260264 A1 | 11/2005 | Edgren et al. | |
| 2006/0104909 A1* | 5/2006 | Vaghefi et al. | ............. 424/10.2 |
| 2007/0031502 A1 | 2/2007 | Pettersson et al. | |
| 2007/0092576 A1* | 4/2007 | Buehler | ..................... 424/489 |
| 2007/0104763 A1* | 5/2007 | Jobdevairakkam et al. | .. 424/441 |

FOREIGN PATENT DOCUMENTS

| | | |
|---|---|---|
| JP | 2000-157168 | 6/2000 |
| WO | 92/14466 | 3/1992 |
| WO | 00/16750 | 3/2000 |
| WO | 2004/026262 | 4/2004 |
| WO | 2005/112896 | 12/2005 |
| WO | 2007/058923 | 5/2007 |

OTHER PUBLICATIONS

Japanese Office Action for Japanese Application No. 2010-537128, mailed Jun. 5, 2013.

* cited by examiner

*Primary Examiner* — Kevin S Orwig
(74) *Attorney, Agent, or Firm* — Morgan, Lewis & Bockius LLP; Christopher J. Betti

(57) ABSTRACT

Novel compositions, formulations and dosage forms comprising stabilized micronized opioid particles are disclosed. Exemplary opioids include oxycodone, oxymorphone, hydrocodone, and hydromorphone, including as free bases or as salts. Stabilized micronized opioid particles having a Dv90 particle size distribution of less and or equal to 10µ or less than or equal to 20µ are disclosed. Methods for micronizing an opioid to provide stabilized micronized opioid particles are also disclosed.

29 Claims, No Drawings

MICRONIZED OPIOID COMPOSITIONS HAVING A SPECIFIC PARTICLE SIZE DISTRIBUTION

CROSS-REFERENCE TO RELATED APPLICATIONS

This application claims priority to U.S. Provisional Application No. 61/012,033, filed on Dec. 6, 2007, and U.S. Provisional Application No. 61/110,855, filed on Nov. 3, 2008, each of which is hereby incorporated by reference in its entirety.

FIELD

The present disclosure relates generally to micronized opioids, including novel compositions, formulations and dosage forms comprising the micronized opioids, as well as methods for their preparation and use. Micronized preparations of opioids, such as oxycodone, and methods of preparing micronized preparations of opioids are useful for the manufacture of stable pharmaceutical products.

BACKGROUND

An opioid is a chemical substance that has morphine-like action in the body. The main therapeutic use of opioids is for pain relief. These agents are thought to work primarily by binding to opioid receptors, which are found principally in the central nervous system and the gastrointestinal tract.

Drug powders containing micron-size drug particles are used in several pharmaceutical dosage forms. Many drugs, especially newly developed substances, are poorly water soluble, which limits their oral bioavailability. This is not true for the salt forms of opioids which are generally soluble. The dissolution rate of insoluble drugs can be enhanced by using micronized drugs. Small drug particles are also required in certain administration forms, which require the drug in micron-size due to the geometric reasons in the organ to be targeted (e.g., drugs for pulmonary use). Again, this is not true for opioids, which are generally administered orally or by injection. The common technique for the preparation of micron-size drugs is the mechanical comminution (e.g., by crushing, grinding, and milling) of previously formed larger particles.

In spite of the use of these techniques, the micronization process can be problematic for the production of small particles because drug substance properties including, for example, surface properties are altered in a mainly uncontrolled manner. For example, the surface of the crystal structure of a micronized particle may be affected in such a manner to make it relatively unstable. In particular, micronized particles may lose their native particle surface crystalline structure by conversion, in varying degrees, to amorphous solid during micronization, upon storage, rendering the particles less stable in their solid state. For example, even the presence of small amounts of an amorphous material in a micronized particle preparation, such as a powder of micronized salbutamol sulfate, has been reported by Brodka-Pfeiffer et al., 2003, Drug Development and Industrial Pharmacy, 29(10):1077-1084, to have deleterious effects on the physical stability of the powder. Amorphous material tends to recrystallize, and lead to particle growth outside a desired particle distribution range in a product including rendering particles unable to reach target tissues or preventing their usefulness in the preparation of pharmaceutical formulations or dosage forms.

SUMMARY

Compositions, formulations and dosage forms comprising stabilized micronized opioid particles are provided. By way of example and not limitation, these opioids include oxycodone, oxymorphone, hydromorphone and hydrocodone. The opioids may be in the form of free bases or salts.

In one aspect, a pharmaceutical composition, formulation or dosage form, particularly a non-aerosol composition, formulation, or dosage form is provided having an active ingredient comprising stabilized micronized opioid particles.

In some embodiments, the stabilized micronized opioid particles comprise a Dv90 particle distribution of less than or equal to about 10μ (micron or μm) or less than or equal to about 20μ. In some embodiments, the stabilized micronized opioid particles comprise a Dv90 particle distribution of less than or equal to about 20μ.

Compositions, formulations and dosage forms are provided that comprise a stabilized micronized opioid particle preparation that does not include a significant amount or population of micronized opioid particles, for example, having a size of less than 1% under 0.2μ. Compositions, formulations and dosage forms include 1μ size particles and up to 20μ size particles, for example, particles less than about 10μ particles, particles less than about 20μ particles, in a matrix or medium in which a homogeneous dispersion of the particles is provided. Among other advantages, a homogeneous dispersion (e.g., substantially uniform or uniform) of micronized particles in a formulation or dosage form can provide for a greater uniformity (e.g., consistency) of release of an opioid from the formulation or dosage form upon in vitro testing and/or in vivo administration.

Preparations of micronized opioid particles of less than or equal to about 10μ or less than or equal to about 20μ and primarily above the nano-particle size range ($10^{-9}$ m) are also advantageous, among other things, for promoting and maintaining the suspension (e.g., substantially uniform or uniform suspension) of the particles within a desired solid, semi-solid or fluid (e.g., liquid) composition, formulation or dosage form, including to maintain the dispersion of particles in the suspension within a fluid composition of formulation or dosage form. Compositions, formulations or dosage forms comprising micronized opioid particles include those that are oral, transdermal, suppository or liquid suspensions. A homogeneous dispersion of micronized opioid particles may provide for a greater uniformity and/or greater stability of the micronized opioid in a formulation or dosage form.

Micronization of the opioid particles according to the present disclosure provides the advantage, among others, of aiding in the suspension (e.g., dispersion) of the opioid particles (e.g., to create a substantially uniform or uniform suspension) during processing in a manufacturing process. In this regard, it is preferred that about 90% of the total particles of the micronized opioid prepared for a dosage form possess a particle size of less than or equal to about 10μ, or less than or equal to about 20μ. Such a micronized opioid particle preparation for manufacturing a product having an appropriate and desired homogeneity of dispersion of the micronized opioid component throughout at least a significant portion of a medium or matrix, for example, a solid, semi-solid, or fluid (e.g., liquid formulation or dosage form) medium or matrix. In addition, having a micronized opioid particle size of less than or equal to about 10μ, or less than or equal to about 20μ is also useful to reduce the occurrence of significant settling of micronized drug particles in a finished formulation or dosage form.

DETAILED DESCRIPTION

The present disclosure provides non-aerosol pharmaceutical preparations in the form of compositions, formulations or dosage forms having as an active ingredient a micronized preparation of an opioid. For example, the micronized opioid preparation is suspended within a fluid medium for a formulation or dosage form.

The present disclosure provides dosage forms comprising formulations having micronized opioid particles, including wherein the micronized opioid particles are suspended within a fluid medium.

Micronization of opioids according to the present disclosure provides an advantage, among others, of facilitating the dispersion and/or suspension of the opioid and/or of promoting uniformity of the opioid in a manufacturing process and/or in a formulation or dosage form. Once uniformly dispersed in a fluid medium or matrix, for example, a liquid and/or a liquefied (e.g., molten) solid, micronized opioids demonstrate retarded (e.g., delayed, reduced) settling. In this regard, it is preferred that at least a significant percentage of the total particles of the micronized opioid prepared for a dosage form possess a particle size of at least about 1μ, less than about 10μ or less than about 20μ. Micronized opioid particle preparations provide for a product having an appropriate and desired homogeneity of dispersion of the micronized opioid component throughout at least a significant portion of a drug formulation medium or matrix, for example, a fluid medium or matrix. In addition, having a micronized opioid particle size of at least about 1μ, less than about 10μ, less than about 20μ provides an advantage, among others, of facilitating the retardation (e.g., delay, reduction) of significant settling of the micronized drug, including in a finished and/or formulated micronized opioid containing product.

Generally, opioids in their salt forms, such as oxycodone HCl, are fairly water soluble. Opioid free bases, such as oxycodone free base, are less soluble and more hydrophobic, and as such may present additional challenges in processing or manufacturing. However, once in the body (e.g., the stomach) opioid free bases are rapidly converted to their salt forms which increases their water solubility. By providing a population of opioid particles in micronized size format within a drug delivery device/capsule/depot/suppository/patch or other delivery form, an advantage of the opioids, including their free base forms, includes an increase in the relative ease of processing during manufacture.

According to the present disclosure, micronization of opioid particles did not change the relative bioavailability of the opioid, as compared to bioavailability of a non-micronized opioid preparation. Hence, a more homogeneous (e.g., more uniform) dispersion of an opioid in a formulation or dosage form may be achieved than was previously possible using the micronized opioid particles, without changing the bioavailability of the opioid, including for example, in a dosage form that is a capsule comprising a fluid (e.g., a liquid such as a highly viscous liquid) formulation in which the micronized opioid particles are dispersed. Accordingly to the present disclosure, formulations and dosage forms with micronized opioid particles are provided that have stability upon storage and retain more predictable and stable release and/or delivery profiles. In addition, an additional advantage of micronization of the opioid is observed in that, because of the reduced particle size, the opioid particles are less susceptible to undesirable settling during manufacturing processes and in formulations or dosage forms of opioid products.

The present disclosure provides compositions, formulations and dosage forms comprising stabilized micronized opioid particles, including preparations of such particles with a Dv90 particle distribution of less than or equal to 10μ or less than or equal to 20μ. Preparations of such particles preferably do not include a significant amount of particles with a particle size distribution under or equal to 0.2μ (e.g., less than or equal to 1% under 0.2μ), or under or equal to 1.0μ (e.g., less than or equal to 10% under 1.0μ).

The present disclosure also provides compositions that comprise micronized opioid particles, wherein at least 90% of the particles have a particle size less than or equal to 10μ, and an additional component such as isopropyl myristate. Optionally the compositions may further comprise triacetin. Such compositions may comprise micronized opioid particles wherein not more than 10% of the particles have a particle size greater than or equal to 0.2μ and less than or equal to 1μ. The compositions may be provided in a liquid suspension or a non-tablet dosage form. Such non-tablet dosage forms may include a capsule, a suppository, a suspension (e.g., oral, otic, ophthalmic, topical, etc.) or a dosage form that is not suitable for inhalation.

Micronized Opioid Compositions, Formulations and Dosage Forms

The present disclosure provides compositions, formulations and dosage forms that comprise stabilized micronized opioid particles. Such compositions, formulations or dosage forms may be non-aerosal or non-sublingual. By way of example and not limitation, micronized opioids may include oxycodone, oxymorphone, hydromorphone and hydrocodone and/or their salts. Additional opioids may include tramadol, fentanyl, sufentanil, remifentanil, tapentadol, naltrexone, nalmefene and naloxone. In some embodiments, compositions, formulations or dosage forms may comprise a high purity opioid, for example, opioids comprising a reduced level of α,β-unsaturated ketones (ABUK) such as at 0.001% or 0.0001% or alternatively, ≤20 ppm. The micronized opioids may be in the form of free bases or salts. The micronized opioids may be highly purified opioids in which impurities of α,β-unsaturated ketones (ABUK) have been substantially removed (e.g., ≤0.003%, ≤0.0025%, ≤0.002%, ≤0.0015%, ≤0.001%, ≤0.0001% w/w ABUK or alternatively ≤30 ppm, ≤25 ppm, ≤20 ppm, ≤15 ppm, ≤10 ppm, ≤5 ppm, ≤3 ppm or ≤1 ppm ABUK). For example, the opioid particles, when the opioid is oxycodone (e.g., oxycodone base or oxycodone HCl), may comprise not more than 0.001% (w/w) or 0.0001% (w/w) 14-hydroxycodeinone or alternatively, ≤20 ppm, ≤15 ppm; ≤10 ppm, ≤5 ppm; ≤3 ppm or ≤1 ppm 14-hydroxycodeinone. For example, the opioid particles, when the opioid is hydrocodone (e.g., hydrocodone base or hydrocodone bitartrate), may comprise not more than 0.025% or 0.0025% codeinone.

In a preferred embodiment, at least a significant percentage of the total particles of the micronized opioid prepared for a dosage form possess a particle size of at least about 1μ, less than about 10μ and less than about 20μ. For example, such a micronized opioid particle preparation may provide for a product having an appropriate and desired homogeneity of dispersion of the micronized opioid component throughout at least a significant portion of a drug formulation medium or matrix, for example, a fluid medium or matrix. In addition, a micronized opioid particle size of at least about 1μ, less than about 10μ, less than about 20μ provides an advantage among others, of facilitating the retardation (e.g., delay, reduction) of significant settling of the micronized drug, including in a finished and/or formulated micronized opioid containing product.

Stabilized micronized opioid particle preparations include micronized opioid particles with targeted and consistent particle size distribution, suitable and/or improved powder flow characteristics without significant particle agglomeration behavior, substantially or essentially free of undesirable physical transformations as compared to a non-micronized preparation of the same opioid. Such stabilized micronized opioid particle preparations are characterized by a stable appearance (white to off-white, fine powder), chemical stability, for example, as measured by HPLC, stable chromatographic purity profile, static water content (e.g., less than about 1.0%, after 12 months stored at 25° C./60% RH) and/or stable distribution of particle size.

Stabilized micronized opioid particle preparations include micronized opioid particles having chemical and/or physical stability upon preparation and/or storage. These stabilized preparations include, for example, micronized opioid particles which upon storage generally resist significant particle size growth (e.g., particle agglomeration or fusion), resist significant formation of impurities and/or degradation products (e.g., oxycodone N-oxide), resist settling within a fluid medium or matrix as compared to non-micronized particles, and/or have improved uniformity of suspension and/or dispersion in a medium (such as a fluid medium) as compared to non-micronized particles, including an enhanced uniformity of suspension and/or dispersion in a fluid or viscous medium and/or enhanced homogeneity of suspension and/or dispersion within a fluid medium as compared to non-micronized particles such as after 3 months, 6 months, 12 months, or even longer under sealed conditions of storage.

Opioid degradation products may include, for example, a compound resulting from a chemical modification of an opioid. The modification, for example, can be the result of a thermally or photochemically induced reaction. Such reactions include, without limitation, oxidation and hydrolysis, as a free base or salt.

Compositions, formulations or dosage forms of the present disclosure may include micronized opioid particles (e.g., stabilized micronized opioid particles with a Dv90 particle distribution of less than or equal to 10μ or a Dv90 particle distribution of less than or equal to 20μ), including high purity opioid particles, and other components, for example, solvents including one or two solvents such as isopropyl myristate and/or triacetin. Such compositions, formulations and dosage forms may include additional components with various properties, for example, components that act as antioxidants such as butylated hydroxytoluene (BHT) or components that act as viscosity modifiers such as colloidal silicon dioxide, cellulose acetate isobutyrate or hydroxyethyl cellulose. Additional components include other liquid or semi-solid lipid systems such as Gelucine. Liquid components may include highly viscous liquids such as sucrose acetate isobutyrate. For example, compositions, formulations and dosage forms (e.g. non-tablet dosage forms) of the present disclosure include liquid compositions, formulations (e.g., suspensions) or dosage forms comprising micronized opioid particles and isopropyl myristate and optionally further comprising triacetin.

Any of a variety of dosage forms and/or delivery methods can be used in conjunction with a composition, formulation or dosage form of the present disclosure. Delivery methods and/or dosage forms suitable for use with the compositions, formulations or dosage forms of the present disclosure can take advantage of any of a variety of drug release mechanisms. For example, dosage forms suitable for use as described herein may be adapted for retaining a quantity of drug formulation (e.g., contained in a drug reservoir or solubilized, suspended or integrated into a vehicle, substrate or matrix such as a polymer, wax, binding solid, liquid etc.) sufficient for treatment, including for a pre-selected period, including for an administration period ranging from one to several hours, one to several weeks, one to several months or up to one or more years. For example, formulations and dosage forms for use as described herein may be adapted for modified release such as immediate, controlled, sustained delayed or targeted release (or combinations thereof). Exemplary dosage forms include drug delivery devices (e.g., drug pumps, including osmotic pumps), implants (e.g., bioerodable implants), sustained release injectables (e.g., injectable liquid formulations, gels including hydrogels such as collagen hydrogels), microparticulate suspensions, microsphere suspensions, liposome formulations, micelle formulations, oil suspensions (including emulsions), wax-based formulations (e.g., suppositories) or encapsulated particulate suspensions. Exemplary drug delivery dosage forms that may be suitable for use with the present disclosure are described in Encyclopedia of Controlled Drug Delivery (1999), Edith Mathiowitz (Ed.), John Wiley & Sons, Inc. A dosage form can be selected from, for example, any of a variety of conventional drug release devices that are conventionally used as an external element (e.g., an external pump) or implanted element of a drug delivery system or oral dosage forms including osmotic dosage forms.

For example, a dosage form (e.g., delivery device) is one that is adapted for delivery of opioids, such as, by way of example and not limitation, oxycodone, oxymorphone, hydromorphone, hydrocodone, as free bases or salts, or any mixture or combination thereof, over an extended or relatively abbreviated period of time. Such delivery devices may be adapted for administration of an opioid over several hours (e.g., 1 hour, 2 hours, 4 hours, 6 hours, 8 hours, 12 hours, or 24 hours to 48 hours or more), to several days (e.g., 2 to 5 days or more, from about 100 days or more), to several months or several years.

The present disclosure provides dosage forms comprising formulations having micronized opioid particles, including wherein the micronized opioid particles are suspended within a fluid medium.

The present disclosure further provides stabilized micronized opioids such as oxycodone that may be formulated to provide many different dosage forms, such as solid, semi-solid, liquid, and semi-liquid preparations, including formulations with waxes or the like. Remington's Pharmaceutical Sciences 20th edition: (ed. Gennard, Alfonso R.) Mack Publishing Company, 1995, specifically incorporated herein by reference, provides technical guidance and information of the various delivery forms and formulations that may be used in conjunction with micronized opioid preparations according to the present disclosure.

Various dosage forms as disclosed herein can be an external, partially implanted, or implanted device (e.g., biodegradable implants or pumps), which can be based on, for example, drug diffusion systems, electrochemical systems, electromechanical systems, osmotic pumps, electrodiffusion systems, electroosmosis systems, vapor pressure pumps, electrolytic pumps, effervescent pumps, piezoelectric pumps, erosion-based systems, diffusive systems and the like.

By way of non-limiting examples, suppositories (such as in a wax medium format), patches (such as for delivery of an opioid alone or together with any abuse resistant component (e.g., naloxone, naltrexone or nalmefene)), capsules, syrups, lotions, creams, and the like may be formulated to include micronized preparations of the opioids as described herein, including for administration for the treatment of pain, including chronic pain and/or to provide pain relief, including for the treatment of moderate to severe pain. By way of non-limiting examples, the following drug delivery forms may be used in the various formulations of the present disclosure to include micronized opioid particles: transdermal/dermal, suppositories, oral suspensions, oral fluids, including encapsulated fluids (e.g., hard gel capsules or soft gel capsules, such as gelatin capsules).

Pharmaceutical compositions can be formulated as transdermal dosage forms, such as a diffusion-driven transdermal system (transdermal patch) using either a fluid reservoir or a drug-in-adhesive matrix system, topical gels, lotions, ointments, transmucosal systems and devices, or iontophoretic (electrical diffusion) delivery systems. Transdermal dosage forms are convenient dosage forms for delivering many different active therapeutically effective agents, including but not limited to, such as for example, opioids such as micronized opioid preparations of the present disclosure. Opioid active agents include, but are not limited to, oxycodone, oxymorphone, hydromorphone, hydrocodone, or any combination thereof and can include an opioid as freebase or salt. Transdermal dosage forms may be particularly useful for timed release and sustained release of active agents, including wherein the active agent comprises a stabilized micronized opioid particle preparation. Transdermal dosage forms may be classified into transdermal dosage articles and transdermal dosage compositions. Common transdermal dosage articles include a diffusion-driven transdermal system (transdermal patch) using either a fluid reservoir or a drug-in-adhesive matrix system. Transdermal dosage compositions include, but are not limited to, topical gels, lotions, ointments, transmucosal systems and devices, and iontophoretic (electrical diffusion) delivery systems. Preferably, the transdermal dosage form is a transdermal patch.

Transdermal dosage forms can include a backing layer made of pharmaceutically acceptable material which is impermeable to stabilized micronized opioid particles. The backing layer preferably serves as a protective cover for the opioid (e.g., oxycodone), and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films, textile fabrics, if the components of the reservoir cannot penetrate the fabric due to their physical properties and the like. Preferably, materials used for a backing layer are laminates of such polymer films with a metal foil such as aluminum foil. A backing layer can be any appropriate thickness which will provide the desired protective and support functions. A suitable thickness will be from about 10μ to about 200μ. Desirable materials and thickness will be apparent to the skilled artisan.

Transdermal delivery systems can include an adhesive layer to affix the dosage form to the skin of the patient for a desired period of administration, (e.g., about 1 to about 5 to 8 hours). If the adhesive layer of a dosage form fails to provide adhesion for the desired period of time, it is possible to maintain contact between the dosage form with the skin by, for instance, affixing the dosage form to the skin of the patient with an adhesive tape, e.g., surgical tape. Adhesion of the dosage form to the skin of the patient can be achieved solely by the adhesive layer of the dosage form or in connection with a peripheral adhesive source, such as surgical tape, but a dosage form is preferably adhered to the patient's skin for the requisite administration period. An adhesive layer can include any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers. An adhesive can be a pressure-sensitive contact adhesive, which is preferably hypoallergenic.

A transdermal dosage form includes a non-permeable backing layer made, for example, of polyester; an adhesive layer made, for example, of a polyacrylate; and a matrix containing a micronized opioid, such as micronized oxycodone, and other desirable pharmaceutical aids such as softeners, permeability enhancers, viscosity agents and the like.

The active agent, in the form of stabilized micronized opioid particles, may be included in the device in a drug reservoir, drug matrix or drug/adhesive layer. For example, the area of a patch, and the amount of active per unit area determine the limit dose, as one of ordinary skill in the art can readily determine.

Certain transdermal delivery systems can also include a softening agent. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids or coconut oil, have proved to be particularly suitable. Further examples of suitable softeners are multivalent alcohols.

A solvent may also be included with micronized opioid particles, such as micronized oxycodone in transdermal delivery systems. Pharmaceutically acceptable compounds that may be included in the reservoir or matrix include: solvents, for example, alcohols such as isopropanol; permeation enhancing agents; or viscosity agents, such as cellulose derivatives, natural or synthetic gums, such as guar gum, and the like.

A transdermal dosage form can include a removable protective layer. Such a removable protective layer is removed prior to application, and consists of materials used for production of a backing layer described above provided that they are rendered removable, for example, by a silicone treatment. Other removable protective layers, for example, include polytetrafluoroethylene, treated paper, allophane, polyvinyl chloride, or the like. Generally, a removable protective layer is in contact with the adhesive layer and provides a convenient means of maintaining the integrity of the adhesive layer until a desired time of application.

A composition of transdermal dosage forms and a type of device are useful, as a composition or device delivers an active agent (e.g., stabilized micronized opioid particles), for a desired time period and at a desired flux rate and/or a desired delivery rate of the transdermal dosage form.

A preparation of an opioid that includes stabilized micronized opioid particles may be formulated within a wax or wax-like material to provide a suppository. Upon solidification at room temperature or cooling, a waxy or wax-like carrier matrix containing a stabilized micronized opioid particle population serves to immobilize the stabilized micronized opioid particles in place. Once administered, such as in a suppository, the waxy carrier can soften and/or melt and release the active agent at the site. For example, where a suppository is created for delivery to an animal (e.g., human) of a composition that includes stabilized micronized opioid particles, an increase in temperature provided by contact with a body surface, such as a mucosal surface, of the animal can serve to soften and/or melt the waxy matrix and release opioid agents to the animal.

A preparation of an opioid that includes stabilized micronized opioid particles may be formulated within an oral suspension. Generally, oral suspension formulations increase in viscosity (get thicker) rather than thinner upon storage. The smaller particle sizes of the presently described opioid particles thus present the advantage, among others, of maintaining a suitable suspension of the opioid for a potentially longer period of time, thus enhancing the desirability of the product as related to uniformity of dosing. For delivery of such product forms, an amount of shaking and/or other dispersive process prior to administration to a patient can be desired and uniformity of dispersion of the active agent can be easily facilitated by stabilized micronized preparations of opioid particles.

Methods of Treatment

Stabilized micronized opioids are useful in methods of treating pain in a subject, including where the methods comprise delivering from a micronized opioid composition, formulation or dosage form containing micronized oxycodone or other opioid or combination of opioids. The micronized opioid composition, formulation or dosage form may be provided in a drug delivery device or a dosage form comprising the micronized opioid. Micronized opioids may be provided to the body of a subject at one or more sites as desired.

Micronized opioids are useful as therapeutic agents. Drug or therapeutic agent or active agent may be used interchangeably and can include any opioid such as oxycodone as free base or salt thereof. For example, reference to an opioid alone or to a selected opioid alone, e.g., reference to micronized oxycodone, can be understood to be only exemplary of the drugs suitable for use in compositions, formulations or dosage forms and is not meant to be limiting in any way.

Subject includes any animal, generally a mammal (e.g., human, canine, feline, equine, bovine, etc.), including, but not limited to, a subject in which treatment, alleviation or management of pain is desired, for example, by administration of an opioid.

Opioids may preferably include oxycodone, oxymorphone, hydromorphone, hydrocodone, including as a free base or salt. Additional opioids may preferably include tramadol, fentanyl, sufentanil, remifentanil, naltrexone, nalmefene and naloxone. Opioids may include alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanil, sufentanil, tapentadol, tramadol, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate, (NTII), naltriben (NTB), nor-binaltorphimine (nor-BNI), β-funaltrexamine (β-FNA), BNTX, cyprodime, ICI-174,864, LY117413, MR2266, etoiphine, DAMGO, CTOP, diprenorphine, naloxone benzoylhydrazone, bremazocine, thylketocyclazocine, U50,488, U69,593, spiradoline, DPDPE, [D-Ala2, Glu4] deltorphin, DSLET, Met-enkephalin, Leu-enkephalin, β-endorphin, dynorphin A, dynorphin B, α-neoendorphin, or an opioid having the same pentacyclic nucleus as nalmefene, naltrexone, buprenorphine, levorphanol, meptazinol, pentazocine, dezocine, or their pharmacologically effective esters or salts. In some embodiments, compositions, formulations or dosage forms may comprise a high purity opioid, for example, opioids comprising a reduced level of α,β-unsaturated ketones (ABUK), including ≤0.003%, ≤0.0025%, ≤0.002%, ≤0.0015%, ≤0.001%, ≤0.0001% w/w ABUK or alternatively ≤30 ppm, ≤25 ppm, ≤20 ppm, ≤15 ppm, ≤10 ppm, ≤5 ppm, ≤3 ppm or ≤1 ppm ABUK. For example, the opioid particles, when the opioid is oxycodone (e.g., oxycodone base or oxycodone HCl), may comprise not more than 0.001% (w/w) or 0.0001% (w/w) 14-hydroxycodeinone or alternatively, ≤20 ppm, ≤15 ppm; ≤10 ppm, ≤5 ppm; ≤3 ppm or ≤1 ppm 14-hydroxycodeinone. For example, the opioid particles, when the opioid is hydrocodone (e.g., hydrocodone base or hydrocodone bitartrate), may comprise not more than 0.025% or 0.0025% codeinone.

Delivery of stabilized micronized opioid may be continuous over a period of time depending on the composition, formulation or dosage form, and can be for a pre-selected administration period ranging from several hours, one to several weeks, one to several months, up to one or more years.

Pain amenable to alleviation and/or treatment includes any type of acute or chronic pain such as moderate to severe pain, including, for example, cancer pain, chronic inflammatory disease pain, neuropathic pain, post-operative pain, iatrogenic pain, complex regional pain syndrome, back pain (e.g., failed-back pain), soft tissue pain, joint pain, bone pain, central pain, injury pain, arthritic pain (e.g., from an arthritic condition such as osteoarthritis or rheumatoid arthritis), hereditary disease, infectious disease, headache, causalgia, hyperesthesia, sympathetic dystrophy, phantom limb syndrome, or denervation.

A therapeutically effective amount of a micronized opioid can refer to an amount of a therapeutic agent (e.g., active agent or drug), such as a composition, formulation or dosage form comprising micronized opioid particles, or a rate or extent of delivery of a therapeutic agent, effective to facilitate a desired therapeutic effect. The precise desired therapeutic effect (e.g., the degree of pain relief, and source of the pain relieved, etc.) will vary according to the condition to be treated, the formulation or dosage form to be administered, and a variety of other factors that are appreciated by those of ordinary skill in the art. For example, a desired therapeutic effect can include suppression, reduction or mitigation of pain in a subject suffering from pain that may be associated with any of a variety of identifiable or unidentifiable etiologies.

Methods for Micronization of an Opioid

The present disclosure provides methods for micronizing an opioid (e.g., oxycodone, oxymorphone, hydrocodone or hydromorphone) to provide a stabilized micronized opioid composition, formulation or dosage form. In some embodiments, the method comprises colliding particles in a composition comprising a non-micronized opioid in an air jet mill in the presence of a grinding gas such as nitrogen gas (e.g., from liquid nitrogen), for a period of time sufficient to provide a composition comprising greater than 50% of a micronized opioid composition, including wherein the micronized composition comprises greater than 50% (such as, in some embodiments, 60%, 70%, 80%, or 90%) of micronized opioid particles having a particle size of less than or equal to about 10μ, or less than or equal to about 20μ.

The micronized opioid particles can be evaluated or tested in a conditioning step, wherein a freshly micronized preparation of micronized opioid particles is subjected to a defined set of conditioning parameters. For example, the conditioning parameters may comprise storage of the particles for a 24 hour period under a defined relative humidity (such as 60% RH), and at a defined temperature (such as 25° C.).

In order to provide the advantages described herein, including improving manufacturing processing and/or stabilization of the composition, formulation or dosage form comprising an opioid in a non-aerosol formulation or dosage form, micronized opioid particles that have a size of less than about 10μ are preferred. Preferred compositions, formulations or dosage forms include micronized opioid particles, wherein the particle size of 90% of the particles are less than 10μ.

Bioavailable can refer to the total amount of a drug substance that is absorbed to be available to provide a desired therapeutic effect after administration of a unit dosage form, as compared to the known reference drug product, as commonly determined and accepted by Governmental Regulatory Agencies, such as the United States FDA. Bioavailability can refer to the extent to which the drug (e.g., opioid analgesic) is absorbed from the unit dosage forms and becomes available at the site of drug action.

Micronized can refer to particles of any agent in which the size of the particle has been reduced to a size of less than a non-micronized form of an agent. Micronized can refer to particles that have been processed by milling to give a desired particle size or obtaining a desired particle size by any other means for producing small particles such as in an air jet mill, where particle bombardment/collision between particles within the preparation function to break the particles apart into smaller particles having a fraction of their original size. For example, where the particle is a particle of an opioid, such as oxycodone, the non-micronized form of the oxycodone particle may have particle size of about 50μ to about 56μ. Therefore, and by way of example, a micronized preparation of oxycodone particles can include oxycodone particles having a size of less than about 50μ to about 56μ. By way of example, such a micronized preparation of oxycodone can comprise a preparation that included 50% or more of the composition by weight of oxycodone particles having a substantially reduced particle size compared to a non-micronized oxycodone preparation. For example, a micronized preparation of oxycodone particles may include a mixture of micronized oxycodone particles having a particle size of equal to or below about 20μ, 10μ, 5μ, 4μ, 3μ, 2μ, or even 1μ, including wherein the size of the micronized oxycodone particle is determined by a laser light methodology. Preferably, the micronized particles do not include a substantial amount of particles less than or equal to 0.2μ (e.g., ≤1% of particles≤0.2μ). The particle size is provided in reference to a non-aerosol opioid particle size. This provides a distinction with opioid particles that have been described in reference to aerosol preparations.

An exemplary manufacturing process for micronization of an exemplary opioid, such as oxycodone, may be briefly summarized as follows. The equipment utilized for micronization includes a material feeder (e.g., a screw feeder) to provide a controlled feed rate of opioid material to the mill and a jet mill (e.g., micronizer) to reduce the particle size of the opioid drug substance. Non-micronized opioid drug substance is obtained and, preferably nitrogen gas (e.g., NF quality) is used to grind and classify drug powder during the micronization process (e.g., selected as the process gas). Nitrogen may protect the opioid drug substance from oxidation and/or to reduce the ignition potential of airborne powder during processing. Nitrogen gas may be generated from a liquid nitrogen source and regulated to supply the volumetric flow and pressure for micronization. In this exemplary process, no materials (e.g., fluid carriers, solvents, reagents, or catalysts) other than the process gas (e.g., nitrogen) are involved in micronization of an opioid, such as oxycodone.

An exemplary process includes the following set-up steps: (a) calibrating the feed rate of non-micronized opioid, such as oxycodone, from the material feeder and; (b) starting the flow of nitrogen gas to the feed injector and grind chamber of the jet mill just prior to initiating the feed of non-micronized opioid, such as oxycodone, to the mill. Micronization of an opioid, such as oxycodone, is accomplished by continuously feeding powder and regulating gas (e.g., nitrogen) pressure to the jet mill, preferably with the following operating parameters: (a) feed rate maintained at a target average rate of 50 grams/minute (range of about 20-60 grams/min); (b) gas (e.g., nitrogen) pressure, feed injector set to a target gauge pressure of 6.7 Bars, (range 5.9-7.6 Bars); and (c) gas (e.g., nitrogen) pressure, grind chamber set to a target gauge pressure of 6.2 Bars, (range 5.4-7.1 Bars). A pressure differential of about 0.3-0.7 Bars between the injector and grind gas pressures is preferably maintained to ensure proper aspiration of the feed material through the jet mill. A second pass or additional passes of micronized material through the jet mill may be performed to achieve desired particle size. The process may be stopped periodically to empty the micronized opioid, such as oxycodone, from the collection containers and bag filters into a bulk storage drum lined with antistatic polyethylene liner. Gas (e.g., nitrogen) flow is preferably maintained for a short time (e.g., approximately 30 seconds) after discontinuing the feed of the opioid, such as oxycodone. Periodically the interior of the mill chamber may be inspected for product build-up, which may be removed as necessary to prevent occlusion of the grinding jets or accumulation within the mill chamber that can affect process performance. A lot representative composite sample may be withdrawn for quality control testing. A single lot of micronized opioid, such as oxycodone, may provide drug substance for multiple formulation lots and/or multiple dosage forms.

The micronizer is preferably a spiral jet mill type and uses energy to generate particle-on-particle impact for attrition. Solid particles may be ground and classified to micron sizes in a single pass. For an opioid, such as oxycodone, high pressure nitrogen is preferably used as the micronization gas (e.g., processing agent). Nitrogen may maintain an inert environment in the mill during operation and/or may reduce the risk of explosion due to airborne dust accumulation. The nitrogen gas is preferably used with the opioid but in the absence of other agents or materials (e.g., fluid carriers, solvents, reagents or catalysts) for the micronization.

While micronization is ongoing, opioid drug substance may be continuously delivered by a screw feeder into the mill inlet hopper and is preferably propelled by nitrogen gas (e.g., as propellant gas) into a grinding zone by means of a product acceleration nozzle. Material may be reduced in size by attrition that occurs from high velocity collisions induced by high pressure nitrogen gas (e.g., as grinding gas) that is supplied through jet ports within the mill. During micronization, particles may be fluidized as they travel at high velocity within the mill, and centripetal force may act to classify the particles by their size. Additionally, the fluidized particles may continuously migrate from greater radial distance toward the center of the mill as their size is being reduced. Particles may be reduced to their ultimate size and travel to the central area of the mill where they may be entrained into the collection container(s) by the gas stream. A filter bag integrated with the product collector may enable separation of material from gas flow.

A Hosokawa Alpine Spiral Jet Mill, Model 50AS is preferably used to manufacture micronized drug substance. The configuration of the jet mill preferably includes: (a) an injector nozzle diameter of 0.9 mm; (b) a grinding chamber diameter of 50.0 mm; (c) multiple nozzles (e.g., two or four); (d) a nozzle diameter of 0.8 mm; and (e) an angle of incidence of 50 degrees. Operating parameters that may be evaluated during optimization of the micronization process include the following: (i) propellant gas (e.g., N2) pressure; (ii) grinding gas (e.g., N2) pressure; (iii) product feed rate; and (iv) injector nozzle clearance.

The effect of injector nozzle clearance may be tested. The injector clearance corresponds to the gap distance between the feed injector nozzle and the venturi orifice through which the opioid drug substance travels just prior to entry into the micronization chamber. Greater clearance enables a greater mass flow rate of opioid drug substance to enter the venturi orifice where the high pressure gas stream (preferably nitrogen) from the injector nozzle propels it into the micronization chamber. Injector clearance is set with bushings that determine the position of the injector nozzle and is established during pre-manufacturing equipment assembly.

Micronization of an opioid, such as oxycodone, may be performed with the injector nozzle clearance set at the default position (e.g., 0 mm, no bushings used) and to progressively larger clearance settings. Minimum and maximum achievable product feed rates may be determined for each of the tested settings. The minimum feed rate may be determined by observation when blowback no longer occurs. Blowback is caused by insufficient loading of material within the mill grinding chamber which results in small amounts of airborne opioid drug substance being expelled from the mill inlet. The feed rate of opioid, such as oxycodone, may be gradually increased and the lowest feed rate that results in the cessation of blowback may be established as a minimum effective feed rate for the process. A maximum feed rate may be determined when product accumulation is observed at the feed inlet, because micronized material is exiting the mill more slowly than the feed rate. The particle size distribution (PSD) of micronized opioid samples taken at each feed rate may be analyzed by laser light scattering. Injector and grinding pressures are preferably set at 6.8 and 6.2 Bars respectively for testing conditions. A summary of exemplary testing results is as follows. When the injector nozzle clearance setting was the default and the minimum feed rate was 20 g/min while the maximum feed rate was 22 g/min, the PSD at the minimum feed rate was Dv10 of 0.7μ, Dv50 of 1.7μ and Dv90 of 6.5μ. When the injector nozzle clearance setting was the default plus 3 mm and the minimum feed rate was 17 g/min while the maximum feed rate was 65 g/min, the PSD at the minimum feed rate was Dv10 of 0.8μ, Dv50 of 1.9μ and Dv90 of 3.3μ while the PSD at maximum feed rate was Dv10 of 0.7μ, Dv50 of 3.1μ and Dv90 of 6.6μ. When the injector nozzle clearance setting was the default plus 6 mm and the minimum feed rate was 14 g/min while the maximum feed rate was 14 g/min, the PSD at the minimum feed rate was Dv10 of 0.8μ, Dv50 of 2.0μ and Dv90 of 5.0μ while the PSD at the maximum feed rate was Dv10 of 0.7μ, Dv50 of 3.9μ and Dv90 of 8.4μ. These results indicate that by increasing the injector nozzle clearance, a greater range of feed rates were achieved while maintaining the ability of the process to meet a micronized opioid particle size specification of Dv90 less than or equal to 10μ.

The effect of processing time may also be tested. Cold welding can occur when hardened product deposits on the interior surface of the mill chamber and can accumulate to such an extent that the grinding jet ports within the mill become occluded and thus negatively impact process performance. The potential for cold welding to occur may be dependent upon the properties of the material being milled. Accumulated product due to cold welding is preferably removed at reasonable intervals during micronization by stopping the process and cleaning the mill chamber. In a test of the extent and/or impact of cold welding, a 4 kg batch of an exemplary opioid such as oxycodone was micronized with operating parameter settings as follows: (a) batch size of 4 kg; (b) injector nozzle clearance of default plus 3 mm; (c) product feed rate of 40 to 50 g/min; (d) grinding pressure of 6.2 Bar; and (e) injector pressure of 6.8 Bar. Samples were taken throughout the run at approximately 500 g intervals and analyzed by laser light scattering. The results showed that only minor cold welding was observed in the grinding chamber with no significant accumulation and without interference to micronization process performance. Particle size distributions of samples taken during the entire span of the process remained consistent. These data indicate that micronization can be run continuously without need for periodic or regular cleaning intervals and without evidence of changing process performance.

An exemplary opioid micronization process using preferably nitrogen gas (e.g., high purity of NF quality) and with preferred operating parameters for multi-kilogram batch sizes included: (a) injector nozzle clearance setting at default, product feed rate of 6 to 20 g/min, grinding pressure of 6.2 Bars and injector pressure of 6.8 to 6.9 Bar (for largest batch size of 20 kg.); injector nozzle clearance setting as default plus 3 mm, product feed rate at target of 50 g/min with range of 20 to 60 g/min, grinding pressure of 6.2 Bars and injector pressure of 6.8 to 6.9 Bars (for largest batch size of 28 kg.); and (c) injector nozzle clearance setting at default plus up to 6 mm, product feed range at target of 50 g/min with range of 6 to 80 g/min, grinding pressure of 6.2 Bar with range of 5.4 to 7.1 and injector pressure of target at 6.7 Bar with range of 5.9 to 7.6. Exemplary micronization processes with high purity oxycodone utilized the parameters of (b) above (for largest batch size of 6 kg) and (c) above (for largest batch size up to 280 kg). A preferred set of operating procedures for micronization, including high purity oxycodone, included: injector nozzle clearance setting at default plus 3 mm, product feed rate of 40 to 50 g/min, grinding pressure of 6.2 Bar and injector pressure of 6.8 Bar (for batch sizes of 28 kg or less).

Stabilized micronized opioid particle preparations include micronized opioid particles with targeted and consistent particle size distribution, suitable and/or improved powder flow characteristics without significant particle agglomeration behavior, substantially or essentially free of undesirable physical transformations as compared to a non-micronized preparation of the same opioid. Such stabilized micronized opioid particle preparations are characterized by a stable appearance (white to off-white, fine powder), chemical stability, for example, as measured by HPLC, stable chromatographic purity profile, static water content (e.g., less than about 1.0%, after 12 months stored at 25° C./60% RH) and/or stable distribution of particle size.

Stabilized micronized opioid particles preparations include micronized opioid particles which upon storage generally resist significant particle size growth or particle agglomeration, resist significant formation of impurities and/or degradation products (e.g., oxycodone N-oxide), resist settling within a fluid medium as compared to non-micronized particles, and/or have improved uniformity of suspension and/or dispersion in a medium (such as a fluid medium) as compared to non-micronized particles, including an enhanced uniformity of suspension and/or dispersion in a fluid or viscous medium and/or enhanced homogeneity of suspension and/or dispersion within a fluid medium as compared to non-micronized particles.

Stabilized micronized opioid particle preparations include micronized opioid particles, including those with or without conditioning after micronization, that are relatively resistant to significant particle growth (e.g., agglomeration or particle fusion) in storage, such as after 3 months, 6 months, 9 months, 12 months, or even longer under sealed conditions of storage.

Stabilized micronized opioid particle preparations include micronized opioid particles having chemical and/or physical stability upon preparation (e.g., with or without conditioning) and/or storage, including storage for 1, 3, 6, 9 and/or 12 or more months. Such preparations may preferably comprise particles with a Dv90 particle distribution of ≤10μ or ≤20μ.

Micronized opioid particles may be conditioned. Conditioned micronized opioid particle preparations include micronized opioid particles that have been subjected to particular process conditions after the opioid particles have been micronized. For example, micronized opioid particles may be conditioned by subjecting the particles to a defined set of conditioning parameters, such as a specific relative humidity (e.g., ambient humidity or 43% RH or 60% RH) for a defined period of time (e.g., 24 hours) at a specific temperature (e.g., 25° C. or 60° C.). Storage conditions of stabilized micronized opioid particle preparations include anti-static/desiccant storage.

This disclosure is further illustrated by the following examples which are provided to facilitate the practice of the disclosed methods. These examples are not intended to limit the scope of the disclosure in any way.

EXAMPLE 1

Opioid preparations, including oxycodone (e.g. oxycodone base or oxycodone hydrochloride), hydromorphone (e.g., hydromorphone base or hydromorphone hydrochloride), hydrocodone (e.g., hydrocodone base or hydrocodone bitartrate), or oxymorphone (e.g., oxymorphone base or oxymorphone hydrochloride), may be micronized using an air jet micronizer. In an exemplary method, micronization of opioid preparations was conducted using a Hosokawa Alpine Spiral Jet Mill 50As with a Schenck Accurate 300 Feeder (Screw Feeder). For example, a feed material comprising a non-micronized opioid is injected into a flat cylindrical grinding chamber, the chamber having nozzles arranged tangentially on a peripheral wall, in the presence of a propellant gas pressure and grinding gas pressure appropriate for providing the desired flow dynamics within the chamber needed to effect collision of the opioid particles with each other. An appropriate speed and pressure of the propellant gas pressure (such as an injector gas pressure of 6.8 Bar) and the grinding gas pressure (such as 6.2 Bar) is applied. Size reduction is accomplished by particle on particle collision and interaction with the chamber wall. In essence, the particles are accelerated in a fast gas stream and reduced by inter-particle collision and/or impact against a solid surface. For the micronization of opioids, an inert gas such as nitrogen gas is used, including, for example, an ultrahigh purity liquid nitrogen cylinder. The larger particles are held in the mill by centrifugal (mass) force, while the fine, micronized particles leave the mill in a gas stream and are collected (drag force).

The design of the 50 mm spiral jet micronization chamber of the Hosokawa Alpine Spiral Jet Mill 50AS includes a flat cylindrical grinding chamber having nozzles arranged tangentially on a peripheral wall, the device having no moving parts within the grinding chamber.

Micronized particles that are less than about 0.1μ or 0.2μ are generally not preferred as part of the present preparations, as they do not provide the most desirable formulation amenable characteristics for providing a homogeneous preparation/product. Therefore, particles in the nano-($10^{-9}$) range are not generally targeted in the present processes and product manufacturing methods and procedures.

For example, micronization of oxycodone base reduced mean particle size 51μ for an exemplary non-micronized sample to a Dv90 of 5-6μ for an exemplary micronized sample. The particle size of an exemplary micronized oxycodone preparation appeared to increase only by a small percentage after 3 months, stored at 25° C./60% RH and 40°/75% RH, for example, from 5-6μ (Dv90, time 0) to 6-11μ (Dv90 at three months). This exemplary stability data provides evidence that the micronized oxycodone preparation comprises stabilized micronized opioid particles.

The smaller particle size of micronized opioid particles, maintained upon storage with desiccation is desirable for the preparation of pharmaceutical formulations and dosage forms. Such a micronized preparation, including micronized oxycodone, is desirable in that it can promote physical stability of opioid formulations and dosage forms including, for example, formulations and dosage forms comprising a fluid medium, by substantially slowing the settling rate through the fluid medium. In addition, a micronized opioid such as oxycodone can act to increase or stabilize dissolution rates of formulations and dosage forms and/or can improve can manufacturing processes including compounding and capsule filling (e.g., in maintaining a uniform dispersion).

An exemplary set of processing parameters that may be used in the methods for preparing a micronized opioid preparation within a Hosokawa Alpine Spiral Jet Mill 50A5 with a Schenck Accurate 300 Feeder (Screw Feeder) include a batch size of 4 kg, an injector clearance of default +3, a feed rate of 40 to 50 g/min, a grinding gas pressure of 6.2 Bar, an injector gas pressure of 6.8 Bar, a screw speed of 300 rpm, and an agitator speed of 500 rpm. Another exemplary set of processing parameters include a batch size of 20 kg, a feed rate of 20 g/min, a grinding gas pressure of 6.2 Bar, and an injector (propellant) gas pressure or 6.9 Bar.

Numerous parameters may be adjusted to vary particle size. A first parameter is the number of nozzles/nozzle size. For example, an increase in the nozzle diameter results in a decrease in particle size. Likewise, an increase in the number of nozzles results in a decrease in particle size. Another parameter that may be adjusted is the angle of incidence of the nozzle(s). A wider angle of incidence results in finer particle size. A third parameter that may be adjusted is the gas pressure. For example, an increase in the grinding or propellant gas pressure results in decreased particle size. An increase in the injector/propellant pressure [increases] the particle size due to shorter residence time in the grinding chamber. If the propellant pressure is too low, product intake will be too poor. If the propellant pressure is too high, product will be blown out of the chute. The propellant gas pressure must be at least the same and preferably higher (~1 Bar) than the grinding gas pressure. Maximum recommended pressure for both propellant gas is 10 Bar with recommended operating pressure of 6 to 8 Bar. Another parameter that may be adjusted is the product feed rate. For example, an increase on the feed rate results in an increase in the particle size. Feed rate is controlled by screw speed and agitator speed.

An exemplary micronization process for an exemplary opioid oxycodone may be summarized as follows. Using a Hosokawa Alpine Spiral Jet Mill 50AS with a Schenck Accurate 300 Feeder (Screw Feeder), a non-micronized opioid is injected into the flat cylindrical grinding chamber. During the process, the injector (propellant) nitrogen gas pressure is established and maintained higher than the grinding nitrogen gas pressure (e.g., 0.3 to 0.7 Bar higher) to obtain constant flow of oxycodone into the Spiral Jet Mill. The larger particles are held in the mill by centrifugal (mass) force, while the fine, micronized particles leave the mill in a gas stream and are collected (drag force). The results of the process is a micronized oxycodone preparation having a reduced particle size, the particle size being less than about 10μ. Immediately following micronization, the micronized oxycodone is packaged in plastic bags with desiccant and then stored in plastic drums to preserve the integrity of the micronized particles. This is necessary to maintain stabilized micronized opioid particle preparations. The micronized opioids, particularly the salt forms such as oxycodone HCl or hydromorphone HCl, are hygroscopic. The immediate packaging with desiccation is required to prevent agglomeration and/or fused particles. For example, the micronized oxydocone is placed into a labeled anti-static bag and secured with a cable or twist tie at the open end of the bag. The anti-static bag is placed into a poly bag with a layer of eight-unit, silica gel, printer, Natrasorb® S Tyvek® four-side seal bag desiccant separating the anti-static bag from the poly bag. The label on the anti-static bag is checked to ensure that it is visible through the poly bag and the poly bag is sealed at its open end. The poly bag is placed in a high density polyethylene (HDPE) drum with a layer of eight-unit, silica gel, printer, Natrasorb® S Tyvek® four-side seal bag desiccant separating the poly bag from the drum. A lid is placed on the open end of the drum and secured using a uniquely numbered security locking tag through a side lever-lock (SSL). Such desiccant packaged and stored micronized oxycodone preparations may be used in manufacturing processes, including in compounding processes for the preparation of various formulations and dosage forms of stabilized micronized oxycodone.

EXAMPLE 2

The particle size distribution for micronized or non-micronized oxycodone freebase useful for exemplary dosage forms may be determined by laser diffraction particle size analysis. In an exemplary method, a Malvern Mastersizer 2000 Laser diffractor using a Hydro 2000 S attachment may be used to determine particle size distribution (PSD). The analysis may be performed in accordance with the following test method. In a first step, a carrier fluid is prepared. A bulk test sample (e.g., approximately 0.75 grams) (e.g., oxycodone base) is added to a one liter flask and wet with five to six drops of 1% Triton X-100. The flask is filled with deionized water until it reaches the one liter mark, stirred for approximately fifteen minutes to produce a saturated solution and filtered through a 0.2μ nylon filter. In a second step, a test sample is prepared and dispersed. An aliquot portion of the bulk mass test sample is added into a scintillation vial (the sample weight adjusted as needed to reach an obscuration of 15-30%) and wet with approximately three milliliters of 1% Triton X-100. The sample is dispersed with twenty milliliters of the saturated solution and sonicated for thirty seconds in a Bransonic 3 sonicator. The sample is examined under the microscope to verify adequate dispersion. In a third step, the sample is analyzed. A Malvern Hydro 2000S recirculator is filled with the saturated solution (prepared in step one). A transfer pipette is used to add the entire sample suspension (prepared in step two) into the carrier fluid bath to obtain an obscuration level in the range of fifteen to thirty percent. Once the proper obscuration range is achieved particle size distribution is measured. The results are expressed as cumulative volume diameter, % less than indicated size (e.g., Dv10 or D[v, 0.10], μ). The micronization yields particle sizes of Dv90=3-5μ for lot 1 and lot 2, down from the Dv90=56μ for the non-micronized sample. As shown in Table 1, the analysis of micronized lot 2 is performed in duplicate and both values are shown.

TABLE 1

Solid-state Properties for Exemplary Oxycodone Lots

| Attribute | Non-micronized | Lot 1 | Lot 2 | Lot 2 (waste) |
|---|---|---|---|---|
| Description | N/A | Powder collected in bin | Powder collected in bin | Powder in post-filter bag |
| Feeding rate (g/min) | N/A | 19.7 | 5.6 | 5.6 |
| Grinding pressure (Bar) | N/A | 6.2 | 5.6 | 5.6 |
| Propellant pressure (Bar) | N/A | 6.7 | 6.4 | 6.4 |
| Particle size: | | | | |
| (Dv10, μ) | 5.7 | 0.5 | 0.5, 0.5 | 0.5, 0.5 |
| (Dv50, μ) | 20.5 | 1.4 | 1.5, 2.2 | 1.6, 2.3 |
| (Dv90, μ) | 55.5 | 3.0 | 3.1, 5.1 | 3.3, 4.9 |
| DSC onset temp. (° C.) | 222 | 222 | 222 | |
| Melting enthalpy (J/g) | 107.8 | 107.6 | 105.7 | |
| XRPD | N/A | No change | No change | |

As a secondary analytical method, the micronized and the non-micronized oxycodone analyzed by laser diffraction with results shown in Table 1, were analyzed by optical microscopy to evaluate particle size and the results are shown in Table 2. Sample aliquots (~50 mg for micronized and ~225 mg for non-micronized) were dispersed in 10 ml of sunflower oil and viewed on a Nikon microscope equipped with a 10× objective. Particle size (mean diameter) was determined using Image Pro® Plus software and expressed as a number % undersize. The particle size values determined by optical microscopy as shown in Table 2 are consistent with the laser diffraction particle size data shown in Table 1.

TABLE 2

Particle-size Analysis by Microscopy of Exemplary Oxycodone Lots

| Attribute | Lot 1 | Lot 2 | Non-micronized |
|---|---|---|---|
| # of particles measured | 5978 | 6650 | 1186 |
| % ≤ 1μ | 30.5 | 25.3 | 21.4 |
| % ≤ 5μ | 92.7 | 92.2 | 50.7 |
| % ≤ 10μ | 99.5 | 99.5 | 69.1 |

Additional laser diffraction particle size analyses are conducted with lot 1 and lot 2. These 500 g micronized lots are prepared in accordance with the method of Example 1 using different feed rates as shown in Table 3. The Dv90 decreased from 51μ to 5-6μ for non-micronized and micronized lot samples, respectively. Differences are not observed in the particle size distribution of the different lots prepared with different feeding rates (Table 3).

TABLE 3

Particle-size for Exemplary Oxycodone Lots

| Lot # | Feed rate (g/min) | Air pressure (Bar) Propellant | Air pressure (Bar) Grinding | Particle size (μ) Dv10 | Particle size (μ) Dv50 | Particle size (μ) Dv90 | Melting point (°C.) | XRPD |
|---|---|---|---|---|---|---|---|---|
| Non-micronized | N/A | N/A | N/A | 4.9 | 20.1 | 50.9 | 223.1 | Reference |
| 1 | 20 | 6.9 | 6.2 | 0.7 | 2.1 | 5.1 | 223.0 | Same as reference |
| 2 | 6 | 6.9 | 6.2 | 0.6 | 2.1 | 5.8 | 222.8 | Same as reference |

The micronized lots are also analyzed by X-ray Powder Diffraction (XRPD). XRPD is performed on a powder Bruker D8 Advance diffractometer from 2-45 2θ angles using the following conditions: divergence slit=0.6 mm, receiving slit=0.1 mm, step size=0.02°, anti-scatter slit=0.6 mm, detector slit=0.6 mm, step time=5 sec. The characteristic peaks with relative intensity>20% are at 8.4, 11.5, 12.4, 15.1, 17.0, and 22.0 2θ angles. By comparing the peak positions of the micronized and non-micronized samples, they have the same 2θ position, suggesting the same polymorph. The peak intensities are consistent between micronized samples, but different when compared to the non-micronized sample. Such variation may be usually due to preferred orientation and/or difference in particle size, shape and density.

The micronized lots may also be analyzed by Differential Scanning Calorimetry (DSC). DSC is performed on a TA instrument Q100 using a heating ramp from 25-235° C. at a rate of 5° C./min. The DSC data for both the micronized and non-micronized lots shows a sharp melting endotherm consistent with a crystalline sample. The flat thermogram up to 220° C. observed indicates that there are no volatiles and no water content in the micronized sample. The sharp endotherm observed is consistent with a crystalline material and the absence of other thermal events proves that there were no polymorph transformations during melting.

The DSC data shows that the melting temperature (the DSC onset temperature) were the same for both the micronized and non-micronized samples. Also, the melting endotherms are sharp and same for the micronized and non-micronized samples. There are no significant differences in the melting enthalpies. The same melting endotherm and heat of fusion for the non-micronized and micronized samples is consistent with no change in crystallinity. Both XRPD and DSC support a crystalline starting material, which does not change during micronization. An exemplary dosage form comprises 40 mg (5.13%) oxycodone base (micronized or non-micronized); 319.6 mg (40.98%) pharmaceutical sucrose acetate isobutyrate (SAIB); 213.1 mg (27.32%) triacetin, USP; 111.0 mg (14.23%) isopropyl myristate, NF (IPM); 37.0 mg (4.74%) cellulose acetate butyrate (CAB) 381-20BP; 44.4 mg (5.69%) hydroxyethyl cellulose (HEC); 14.8 mg (1.90%) colloidal silicone dioxide; and 0.16 mg (0.02%) butylated hydroxytoluene (BHT). Additional exemplary dosage forms, such as capsules of different strengths, may comprise opioids, for example, 5 mg, 10 mg, 20 mg, 30 mg, or 40 mg of an opioid and excipients in the following % w/w: 5.13% Opioid (e.g., oxycodone, oxymorphone, hydrocodone or hydromorphone) either as base or salt (micronized or non-micronized); 40.98% Pharmaceutical Sucrose Acetate Isobutyrate (SAIB); 27.32% Triacetin, USP; 14.23% Isopropyl Myristate, NF (IPM); 4.74% Cellulose acetate butyrate, NF/EP, ethanol washed (e.g., grade 381-20 BP); 5.69% Hydroxyethyl cellulose, NF; 1.90% Colloidal silicon dioxide, NF; and 0.02% Butylated hydroxytoluene, NF. For example, for a 60 mg or 80 mg capsule dosage form, the following alternative % w/w may be prepared and used as described herein (a) 10.26% Opioid (e.g., oxycodone, oxymorphone, hydrocodone or hydromorphone) either as base or salt (micronized or non-micronized); 36.21% Pharmaceutical Sucrose Acetate Isobutyrate (SAIB); 26.82% Triacetin, USP; 14.36% Isopropyl Myristate, NF; 4.94% Cellulose acetate butyrate, NF/EP, ethanol washed (e.g., grade 381-20 BP); 5.38% Hydroxyethyl cellulose, NF; 2.02% Colloidal silicon dioxide, NF; and 0.02% Butylated hydroxytoluene, NF; or (b) 10.26% Opioid (e.g., oxycodone, oxymorphone, hydrocodone or hydromorphone) either as base or salt (micronized or non-micronized); 36.46% Pharmaceutical Sucrose Acetate Isobutyrate (SAIB); 27.01% Triacetin, USP; 14.36% Isopropyl Myristate, NF; 5.38% Cellulose acetate butyrate, NF/EP, ethanol washed (e.g., grade 381-20 BP); 2.69% Hydroxyethyl cellulose, NF; 2.02% Colloidal silicon dioxide, NF; 1.79% Gelucire (e.g., 44/14), EP/NF; and 0.02% Butylated hydroxytoluene, NF.

EXAMPLE 3

Samples of Example 2 and additional samples comprising micronized and non-micronized oxycodone useful for exemplary dosage forms are tested for their chemical stability and physical stability. Based on a comparison of stability data from micronized and non-micronized samples stored at both 25° C./60% RH and 40 C.°/75% RH, no differences are observed in the impurity profile through three months of study as shown in Tables 4 and 5 for exemplary lots. The impurities analyzed include (HOXY), 14-Hydroxycodeinone; (DHOXYN), 7,8-Dihydro-8,14-Dihydroxycodeinone; (DHOXY), 7,8-Dihydro-14-hydroxycodeine; (OXYE), Oxycodone ethylenolate; (OXYN), 1-Hydroxyoxycodone and Oxycodone N-oxide. Most of the impurities are found to be below the limit of quantitation (LOQ), except for HOXY and DHOXYN which were unchanged at 0.1%. The potency assay is 99.2-100.7% for the micronized samples and 99.5-101.1% for the non-micronized lots. The solid state stability of the micronized oxycodone is monitored for particle size, XRPD, DSC, and microscopy as shown in Table 6.

TABLE 4

Chemical Stability of Micronized Oxycodone Free Base

| Attribute (%) | Lot 2 Time 0 | Lot 2 1 mo | Lot 2 3 mo | Lot 1 Time 0 | Lot 1 1 mo | Lot 1 3 mo | Lot 3 Time 0 | Lot 3 1 mo | Lot 3 3 mo |
|---|---|---|---|---|---|---|---|---|---|
| Assay | | | | | | | | | |
| 25° C./60% RH | 100.7 | 99.8 | 99.8 | 99.3 | 98.9 | 99.9 | 100.4 | 98.5 | 98.5 |
| 40° C./75% RH | | 99.6 | 99.2 | | 100.0 | 99.5 | | 100.1 | 99.5 |
| Total impurities | | | | | | | | | |
| 25° C./60% RH | 0.18 | 0.18 | 0.18 | 0.18 | 0.18 | 0.18 | 0.18 | 0.18 | 0.18 |
| 40° C./75% RH | | 0.18 | 0.18 | | 0.18 | 0.18 | | 0.18 | 0.18 |
| HOXY | | | | | | | | | |
| 25° C./60% RH | 0.08 | 0.08 | 0.08 | 0.08 | 0.08 | 0.08 | 0.07 | 0.08 | 0.08 |
| 40° C./75% RH | | 0.08 | 0.08 | | 0.08 | 0.08 | | 0.08 | 0.08 |
| DHOXY | | | | | | | | | |
| 25° C./60% RH | <LOQ | <LOQ | <LOQ | <LOQ | <LOQ | <LOQ | <LOQ | <LOQ | <LOQ |
| 40° C./75% RH | | <LOQ | <LOQ | | <LOQ | <LOQ | | <LOQ | <LOQ |
| DHOXYN | | | | | | | | | |
| 25° C./60% RH | 0.10 | 0.10 | 0.10 | 0.10 | 0.10 | 0.10 | 0.11 | 0.10 | 0.10 |
| 40° C./75% RH | | 0.10 | 0.10 | | 0.10 | 0.10 | | 0.10 | 0.10 |
| OXYE | | | | | | | | | |
| 25° C./60% RH | <LOQ | <LOQ | <LOQ | <LOQ | <LOQ | <LOQ | <LOQ | <LOQ | <LOQ |
| 40° C./75% RH | | <LOQ | <LOQ | | <LOQ | <LOQ | | <LOQ | <LOQ |
| 1-HydroxyOXY | | | | | | | | | |
| 5° C./60% RH | <LOQ | <LOQ | <LOQ | <LOQ | <LOQ | <LOQ | <LOQ | <LOQ | <LOQ |
| 40° C./75% RH | | <LOQ | <LOQ | | <LOQ | <LOQ | | <LOQ | <LOQ |
| OXYN | | | | | | | | | |
| 25° C./60% RH | <LOQ | <LOQ | <LOQ | <LOQ | <LOQ | <LOQ | <LOQ | <LOQ | <LOQ |
| 40° C./75% RH | | <LOQ | <LOQ | | <LOQ | <LOQ | | <LOQ | <LOQ |
| Other | | | | | | | | | |
| 25° C./60% RH | <LOQ | <LOQ | <LOQ | <LOQ | <LOQ | <LOQ | <LOQ | <LOQ | <LOQ |
| 40° C./75% RH | | <LOQ | <LOQ | | <LOQ | <LOQ | | <LOQ | <LOQ |

TABLE 5

Chemical Stability of Non-micronized Oxycodone Free Base

| Attribute (%) | Time 0 | 1 mo 25° C./60% RH | 1 mo 40° C./75% RH | 3 mo 25° C./60% RH | 3 mo 40° C./75% RH |
|---|---|---|---|---|---|
| Assay | 101.1 | 99.6 | 99.6 | 99.6 | 99.5 |
| Total impurities | 0.18 | 0.18 | 0.18 | 0.18 | 0.18 |
| HOXY | 0.08 | 0.08 | 0.08 | 0.08 | 0.08 |
| DHOXY | <LOQ | <LOQ | <LOQ | <LOQ | <LOQ |
| DHOXYN | 0.10 | 0.10 | 0.10 | 0.10 | 0.10 |
| OXYE | <LOQ | <LOQ | <LOQ | <LOQ | <LOQ |
| 1-HydroxyOXY | <LOQ | <LOQ | <LOQ | <LOQ | <LOQ |
| OXYN | <LOQ | <LOQ | <LOQ | <LOQ | <LOQ |
| Other (>0.05%) | <LOQ | <LOQ | | <LOQ | <LOQ |

TABLE 6

Physical Stability of Micronized Oxycodone Free Base

| Attribute | Lot 2 | | Lot 1 | | Lot 3 | |
|---|---|---|---|---|---|---|
| | Time 0 | 3 mo | Time 0 | 3 mo | Time 0 | 3 mo |
| Particle size (Dv90, μ) | | | | | | |
| 25° C./60% RH | 4 | 10 | 4 | 6 | 6 | 10 |
| 40° C./75% RH | | 10 | | 11 | 6 | 11 |
| XRPD | | | | | | |
| 25° C./60% RH | Same as reference[a] | Same as reference | Same as reference | Same as reference | Same as reference | Same as reference |
| 40° C./75% RH | Same as reference | Same as reference | Same as reference | Same as reference | Same as reference | Same as reference |
| DSC Onset Melt (° C.) | | | | | | |
| 25° C./60% RH | 221.8 | 221.8 | 222.0 | 221.8 | | 221.9 |
| 40° C./75% RH | | 221.9 | | 221.9 | | 221.9 |
| Microscopy, ≤10 μ %) | | | | | | |
| 25° C./60% RH | 99.5 | 99.5 | 99.5 | 98.4 | | 98.3 |
| 40° C./75% RH | | 98.3 | | 98.2 | | 94.5 |

[a]XRPD of the non-micronized lot.

When Lot 3 was stored at 25° C./60% RH and additionally tested for stability at 1, 6, 9 and 12 months, the particle size (Dv90) was 9μ, 10μ, 8μ and 8μ, respectively. When Lot 3 was stored at 40° C./75% RH and additionally tested at 1 and 6 months, the particle size (Dv90) was 9μ and 10μ, respectively.

Additional lots of opioid were prepared. Three large scale lots of oxycodone base (e.g. 28 kg, 28 kg, 25.9 kg) were micronized, packaged in desiccant (see, e.g., Example 1) and stored at 25° C./60% RH. When these micronized lots were tested for stability at 0, 6, 9 and 12 months, the particle size (Dv90): for the first lot was 6μ, 7μ, 6μ and 7μ, respectively; for the second lot was 4μ, 5μ, 6μ and 6μ, respectively; and for the third lot was 4μ, 6μ, 6μ and 7μ, respectively. The ABUK (e.g. 14-hydroxycodeinone) concentration was 0.07% or 0.08% (w/w) throughout the stability testing. Three lots of high purity oxycodone base (e.g., 6 kg each) with no more than 0.001% ABUK (e.g., 14-hydroxycodeinone) were micronized, packaged in desiccant (see, e.g., Example 1) and stored, including at 25° C./60% RH and/or 40° C./75% RH. When these high purity micronized lots were tested for stability at 0, 1, 3, 6, 9 and 12 months, the particle size (Dv90): for the first high purity lot was 4μ, 5μ, 5μ, 5μ, 6μ and 6μ, respectively; for the second high purity lot was 4μ, 4μ, 4μ, 5μ, 5μ and 5μ, respectively; for the third high purity lot was 5μ, 4μ, 4μ, 5μ, 5μ, and 5μ, respectively. When these high purity micronized lots were stored at 25° C./60% RH and tested for stability at 0, 1, 3, 6, 9 and 12 months, the particle size (Dv90): for the first high purity micronized lot was 4μ, 4μ, 5μ, 5μ, 7μ and 6μ, respectively; for the second high purity micronized lot was 4μ, 4μ, 4μ, 6μ, 5μ and 6μ, respectively; and for the third high purity micronized lot was 5μ, 4μ, 4μ, 5μ, 5μ and 5μ, respectively. When these high purity micronized lots were stored at 40° C./75% RH and tested for stability at 0, 1, 3 and 6 months, the particle size distribution (Dv90): for the first high purity micronized lot was 4μ, 5μ, 5μ and 5μ, respectively; for the second high purity micronized lot was 4μ, 5μ, 5μ and 6μ, respectively; and for the third high purity micronized lot was 5μ, 4μ, 5μ and 5μ, respectively.

EXAMPLE 4

Micronization of a hydromorphone HCl preparation may be conducted using a Spiral Jet Mill and screw feeder apparatus as described in Example 2. The particle size distribution for micronized or non-micronized hydromorphone HCl may be determined by laser diffraction particle size analysis according to an exemplary method similar to that described in Example 2, except that the Malvern Hydro 2000S recirculator is filled with a 2% lecithin in Isopar G solution, the scintillation vial is filled with approximately 20 ml of 2% lecithin in Isopar G solution, ultrasonication of the sample preparation is for 15 seconds and the sample suspension is added into the carrier fluid bath to obtain an obscuration level in the range of 10 to 20%.

In an exemplary micronization method, the feed hopper is loaded with hydromorphone HCl (e.g., 500 mg lot) and micronization of hydromorphone HCl is conducted with the Spiral Jet Mill described in Example 1. For the initiation of a milling sequence, the grinder chamber diameter is 50 mm, the nozzle ring is set at 50 degrees, 4×0.8 mm, the injector nozzle diameter is 0.9 mm, the gap setting is +3 mm. The target feed rate is 50 g/min. The injector gas pressure is approximately 0.3-0.7 Bar higher than grinding gas pressure to obtain constant draw of hydroxymorphone HCl into the Spiral Jet Mill, chamber, for example, an injector gas pressure is 5.5 Bar and grinding gas pressure is 4.8 Bar.

Hydromorphone HCl is micronized with compressed $N_2$ gas at 70 psi and 50 g/min feed rate, for a total of three runs. Even when micronization of hydromorphone HCl is followed immediately by storage under desiccation as described in Example 1, instability of particles leading to non-dispersed, aggregated or clumped materials is observed. Conditioning studies are designed to increase the stability of the hydromorphone HCl. Three runs are used for conditioning studies. From a 500 gram non-micronized sample, 450 grams micronized is obtained. About 60 grams is immediately compounded for preparation of a micronized hydromorphone formulation and dosage form. The remaining amount is placed into antistatic/desiccant storage as described in Example 1.

TABLE 7

| | Pre-storage 24 hours Conditioning of Hydromorphone HCl | | | |
|---|---|---|---|---|
| Condition 1 No Conditioning | Condition 2 25° C./vacuum/ desiccant | Condition 3 25° C./43% RH Sat. K2CO3 | Condition 4 25° C./60% RH Stab. Chamber | Condition 5 60° C./ambient humidity |
| Group #1 Group #6 | Group #2 Group #7 | Group #3 Group #8 | Group #4 Group #9 | Group #5 Group #10 |

Micronized samples from the above batches (e.g., 125 grams) are obtained on the same day the samples are micronized and samples of the non-micronized starting material (e.g., 125 grams) are used for the conditioning studies as described in Table 7 (Group 1-5 micronized and Group 6-10 non-micronized). Results of exemplary conditioning studies show that, for example, a Condition 5 treatment as shown in Table 7 yields a stabilized micronized hydromorphone HCl preparation. An exemplary non-micronized hydromorphone HCl preparation has a Dv90 of 226μ, a Dv50 of 116μ and a Dv10 of 26μ. An exemplary micronized hydromorphone HCl preparation with conditioning for 24 hours at 60° C. (Condition 5 in Table 7) and stored under desiccation at ambient temperature as described in Example 1, has a Dv90 of 11.2μ, a Dv50 of 4.7μ and a Dv10 of 0.8μ. When the micronized preparation is put under stability test conditions of 25° C./60% RH for 3 months, the Dv90 is 11.2μ, the Dv50 is 4.5μ and the Dv10 is 0.8μ and for 12 months, the Dv90 is 10.5μ, the Dv50 is 4.4μ and the Dv10 is 0.8μ. When the micronized preparation is put under stability test conditions of 40° C./75% RH for 3 months, the Dv90 is 17.1μ, the Dv50 is 8.4μ and the Dv10 is 0.9μ and for 12 months, the Dv90 is 16.5μ, the Dv50 is 8μ and the Dv10 is 0.8μ. Thus, when the micronized preparation that was micronized followed by conditioning is stored for multiple months (e.g., 3 months and 12 months) and tested, the particle size is stabilized and is less than or equal to 20μ under testing conditions of long term stability (25° C./60% RH) or accelerated stability (40° C./75% RH).

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

The invention claimed is:

1. A non-aerosol pharmaceutical formulation comprising stabilized micronized oxycodone free base particles, wherein the oxycodone free base particles have a $DV_{90}$ particle size distribution of 3 μm to 6 μm, a $DV_{50}$ particle size distribution of 1.4 μm to 2.2 μm, and a $DV_{10}$ particle size distribution of 0.5 μm to 0.7 μm.

2. The non-aerosol pharmaceutical formulation of claim 1, wherein the particles are in a fluid medium.

3. The non-aerosol pharmaceutical formulation of claim 1, wherein the formulation is suitable for oral administration.

4. The non-aerosol pharmaceutical formulation of claim 1 wherein the formulation is suitable for transdermal administration.

5. The non-aerosol pharmaceutical formulation of claim 1 wherein the formulation is suitable for suppository administration.

6. The non-aerosol pharmaceutical formulation of claim 1 wherein the formulation is suitable for parenteral administration.

7. The non-aerosol pharmaceutical formulation of claim 1, wherein the formulation further comprises an excipient.

8. The non-aerosol pharmaceutical formulation of claim 1, wherein the excipient is a solvent.

9. The non-aerosol pharmaceutical formulation of claim 8, wherein the solvent is a hydrophilic solvent.

10. The non-aerosol pharmaceutical formulation of claim 8 wherein the solvent is a hydrophobic solvent.

11. The non-aerosol pharmaceutical formulation of claim 7 wherein the excipient is an anti-oxidant.

12. An oral dosage form comprising stabilized micronized oxycodone free base particles with a $DV_{90}$ particle size distribution of 3 μm to 6 μm, a $DV_{50}$ particle size distribution of 1.4 μm to 2.2 μm, and a $DV_{10}$ particle size distribution of 0.5 μm to 0.7 μm; and a fluid medium, wherein the stabilized micronized oxycodone free base particles are dispersed within the fluid medium.

13. The oral dosage form of claim 12 further comprising an excipient.

14. The oral dosage form of claim 13, wherein the excipient is a solvent.

15. The oral dosage form of claim 14, wherein the solvent is a hydrophilic solvent.

16. The oral dosage form of claim 14 wherein the solvent is a hydrophobic solvent.

17. The oral dosage form of claim 12 comprising 5 mg, 10 mg, 20 mg, 30 mg or 40 mg of oxycodone free base.

18. The oral dosage form of claim 12 further comprising a suspending agent.

19. The oral dosage form of claim 12 further comprising a polymer.

20. A drug delivery form comprising stabilized micronized oxycodone free base particles with a $DV_{90}$ particle size distribution of 3 μm to 6 μm, a $DV_{50}$ particle size distribution of 1.4 μm to 2.2 μm, and a $DV_{10}$ particle size distribution of 0.5 μm to 0.7 μm in a liquid, semi-liquid, or waxy medium.

21. The drug delivery form of claim 20 wherein the drug delivery form is a transdermal patch, suppository, lotion, cream, ointment, gel, implant or pump.

22. The non-aerosol pharmaceutical formulation of claim 1, wherein the stabilized micronized oxycodone free base particles have a $DV_{90}$ particle size distribution of 3 μm to 5 μm.

23. The non-aerosol pharmaceutical formulation of claim 1, wherein the stabilized micronized oxycodone free base particles have a $DV_{90}$ particle size distribution of 5 μm to 6 μm.

24. The oral dosage form of claim 12, wherein the stabilized micronized oxycodone free base particles have a $DV_{90}$ particle size distribution of 3 μm to 5 μm.

25. The oral dosage form of claim 12, wherein the stabilized micronized oxycodone free base particles have a $DV_{90}$ particle size distribution of 5 μm to 6 μm.

26. The drug delivery form of claim 20, wherein the stabilized micronized oxycodone free base particles have a $DV_{90}$ particle size distribution of 3 μm to 5 μm.

27. The drug delivery form of claim 20, wherein the stabilized micronized oxycodone free base particles have a $DV_{90}$ particle size distribution of 5 μm to 6 μm.

28. The oral dosage form of claim 12, wherein the stabilized micronized oxycodone free base particles are uniformly dispersed within the fluid medium.

29. The non-aerosol pharmaceutical formulation of claim 1, wherein ≤1% of the stabilized micronized oxycodone free base particles have a particle size ≤0.2 μm.

* * * * *